(12) United States Patent
Kavolus, II et al.

(10) Patent No.: US 11,285,007 B2
(45) Date of Patent: Mar. 29, 2022

(54) JOINT IMPLANT

(71) Applicants: Joseph John Kavolus, II, Brookline, MA (US); William Abbott Byrd, Nashville, TN (US)

(72) Inventors: Joseph John Kavolus, II, Brookline, MA (US); William Abbott Byrd, Nashville, TN (US)

( * ) Notice: Subject to any disclaimer, the term of this patent is extended or adjusted under 35 U.S.C. 154(b) by 66 days.

(21) Appl. No.: 16/594,554

(22) Filed: Oct. 7, 2019

(65) Prior Publication Data
US 2020/0129298 A1 Apr. 30, 2020

Related U.S. Application Data

(60) Provisional application No. 62/751,746, filed on Oct. 29, 2018.

(51) Int. Cl.
| | | |
|---|---|---|
| *A61F 2/36* | (2006.01) | |
| *C08L 23/06* | (2006.01) | |
| *A61F 2/30* | (2006.01) | |

(52) U.S. Cl.
CPC ............ *A61F 2/3609* (2013.01); *C08L 23/06* (2013.01); *A61F 2002/30663* (2013.01);
(Continued)

(58) Field of Classification Search
CPC .......... A61F 2/3609; A61F 2002/30663; A61F 2310/00203; A61F 2310/00257;
(Continued)

(56) References Cited

U.S. PATENT DOCUMENTS 4,978,355 A * 12/1990 Frey .................... A61F 2/30907
623/23.54
5,066,304 A 11/1991 Crowninshield et al.
(Continued)

FOREIGN PATENT DOCUMENTS

| CN | 105030378 A | 11/2015 |
|---|---|---|
| EP | 0768066 A2 | 4/1997 |
| EP | 1582182 A1 | 10/2005 |

OTHER PUBLICATIONS

Hernigou, P., et al., International Orthopaedics (SICOT) (2013) 37:2081-2088, "One hundred and fifty years of history of the Morse taper: from Stephen A. Morse in 1864 to complications related to modularity in hip arthroplasty".
(Continued)

*Primary Examiner* — Jerrah Edwards
*Assistant Examiner* — Jared Klar Rovira
(74) *Attorney, Agent, or Firm* — Dority & Manning, P.A.

(57) ABSTRACT

The present disclosure relates generally to the field of mammalian prosthetics, and more specifically to prostheses for use in total or partial joint replacement, and to a method of use of these prostheses in arthroplasty. Thus, disclosed is a prosthesis for use in hip arthroplasty that comprises an artificial femoral head that includes a head portion constructed totally or partially of a polymeric material, and a connector means designed to connect said head portion in a non-articulating manner to a femoral stem portion. The head portion may be made solely of solid polymeric material or of an outer shell of polymeric material connected in a non-articulating manner to an embedded core. The polymeric material is preferably selected from ultra-high molecular weight polyethylene (UHMWPE) or radiation treated UHMWPE having substantially no detectable free radicals. The embedded core comprises, for example, one or more of solid non-polymeric material (e.g., metallic,
(Continued)

ceramic, or ceramic-on-metal material), a multiplicity of metallic spokes, a metallic scaffolding, and/or combinations thereof.

24 Claims, 8 Drawing Sheets

(52) U.S. Cl.
CPC ............ *A61F 2002/3615* (2013.01); *A61F 2310/00017* (2013.01); *A61F 2310/00023* (2013.01); *A61F 2310/00029* (2013.01); *A61F 2310/00203* (2013.01); *A61F 2310/00239* (2013.01); *A61F 2310/00257* (2013.01); *C08L 2207/068* (2013.01)

(58) Field of Classification Search
CPC .. A61F 2310/00029; A61F 2310/00017; A61F 2002/3615; A61F 2310/00239; A61F 2310/00023; A61F 2002/365; A61F 2002/30971; A61F 2002/30973; A61F 2002/30957; A61F 2002/30408; A61F 2002/30332; C08L 23/06; C08L 2207/068
See application file for complete search history.

(56) References Cited

U.S. PATENT DOCUMENTS

| | | | |
|---|---|---|---|
| 5,180,394 A | 1/1993 | Davidson | |
| 8,357,205 B2 | 1/2013 | Rahaman et al. | |
| 8,529,633 B2 | 9/2013 | Lazennec et al. | |
| 9,192,478 B2 | 11/2015 | Weeden | |
| 2002/0015653 A1 | 2/2002 | Weisener et al. | |
| 2002/0147499 A1 | 10/2002 | Shea et al. | |
| 2003/0120347 A1 | 6/2003 | Steinberg | |
| 2006/0259148 A1 | 11/2006 | Bar-Ziv | |
| 2009/0157189 A1* | 6/2009 | Hartman | B28B 1/24 623/18.11 |
| 2010/0262144 A1 | 10/2010 | Kelman et al. | |
| 2014/0094927 A1* | 4/2014 | Weeden | A61F 2/34 623/22.21 |
| 2016/0029952 A1 | 2/2016 | Hunter | |
| 2016/0287395 A1 | 10/2016 | Khalili et al. | |
| 2017/0035571 A1* | 2/2017 | Loffredo | A61F 2/3603 |

OTHER PUBLICATIONS

Van der Merwe, J. M., J. Am. Acad. Orthop. Surg. 2018;26:479-488, "Comprehensive Review of Current Constraining Devices in Total Hip Arthroplasty".

De Martino, et al., World J Orthop Jul. 18, 2014; 5(3): 180-187, "Dual mobility cups in total hip arthroplasty".

Stryker Technical Publication, 2013, "MDM® X3® Modular Dual Mobility Acetabular System".

Kyomoto, M., et al., Biomaterials, vol. 31, Issue 4, Feb. 2010, pp. 658-668, "Lubricity and stability of poly(2-methacryloyloxyethyl phosphorylcholine) polymer layer on Co—Cr—Mo surface for hemi-arthroplasty to prevent degeneration of articular cartilage", Abstract Only.

* cited by examiner

JOINT IMPLANT

CROSS-REFERENCE TO RELATED APPLICATIONS

This application claims priority under 35 USC § 119(e) to U.S. Provisional Patent Application Ser. No. 62/751,746, filed on Oct. 29, 2018, the disclosure of which is incorporated herein by reference in its entirety.

FIELD OF INVENTION

The present disclosure relates generally to the field of mammalian prosthetics. More specifically, it relates to prostheses for use in total or partial joint replacement and to associated methods of use of these prostheses in arthroplasty.

BACKGROUND OF INVENTION

Although the invention disclosed in the following pertains primarily to prostheses for use in total or partial replacement of hip joints and to associated methods of use of these prostheses in hip arthroplasty, it is to be understood that, as contemplated herein, the invention may have usefulness in similar prostheses for arthroplasty of other mammalian joints as well, such as, illustratively, shoulder joints.

Hip replacement is a surgical procedure in which the hip joint is replaced by a prosthetic implant, that is, a hip prosthesis. Hip replacement surgery can be performed as a total replacement or a partial replacement, also referred to as hemi (half) replacement. Such hip joint replacement orthopedic surgery is generally conducted to relieve arthritis pain or to repair damage that may be present due to osteoarthritis or resulting from hip fractures. A total hip replacement (total hip arthroplasty) usually consists of replacing both the acetabulum (e.g., with a metal cup) and the proximal femur and/or femoral head (e.g., with an artificial pivoting ball); while hemiarthroplasty generally only replaces the femoral head. The artificial femoral head thus articulates in the acetabular cup to form a "ball and socket" joint. The average cost of a total hip replacement in 2012 was $40,364 in the United States, and about $7,700 to $12,000 in most European countries.

Total hip arthroplasty has become one of the most successful, and currently one of the most common, modern operative procedures. Not too long ago, it was hailed in the medical journal *The Lancet* as "The Operation of the Century." However, despite its wild acclaim and success, short-term and long-term patient satisfaction continue to vary widely. Three major issues that plague the procedure remain. The most devastating issue is infection, followed by the issue of instability of the joint leading to hip dislocation after the procedure, and finally the issue of wear of the implants. In the late 1990s and the early 2000s, metal-on-metal hip replacements were hailed as a triumph of two of these concerns, namely dislocation and wear. The thought was that the larger diameter heads of the metal replacements would decrease the possibility of dislocations (which was indeed the case), while the metal-on-metal articulation would be recalcitrant to the wear encountered with metal-on-plastic hip implants. Inevitably, it has been reported that the metal-on-metal articulation, while producing less linear wear of the prosthesis, which in the lab correlated to improved longevity and cycles, did create a high amount of smaller metal ions as a result of "volumetric wear." This results in violent soft tissue reactions, largely mediated by the patient's immune system, causing local tissue destruction. This issue has ultimately resulted in recall of these metal-on-metal implants from the market.

Around the same time that metal-on-metal implants were experiencing their rise and fall, the advent of highly cross-linked polyethylene in total hip replacement provided a metal-on-plastic articulation. These implants were more resistant to wear, improving the longevity of the implants in question and decreasing the catastrophic osteolysis that is correlated with the particulate debris from accelerated wear of the early generation polyethylene implants. However, one major drawback of the metal-on-polyethylene implants was that the size of the artificial femoral head could not be as large as with a metal-on-metal articulation. The newer generation polyethylene liners could be thinner owing to their improved wear characteristics, which allowed for the widespread adoption of 40-32 mm metal or ceramic femoral heads as opposed to 28-22 mm heads of the earliest generation hip replacements. The increase in head diameter and head neck offset of these larger diameter heads have increased the jump distance for dislocation and decreased impingement related dislocation to a rate of approximately 2% in primary total hip replacement and up to 10-30% in revision procedures. However, these numbers are greater than the largest diameter metal-on-metal hip articulations, where femoral head diameter could reach greater than 48 mm. To date these implants (in the absence of soft tissue reaction) exhibit the lowest dislocation rates (<1%); but, again due to their catastrophic failure mechanism they have largely been abandoned.

In an effort to seize upon the advantages of the large diameter head without abandoning the (to date) reliable metal-on-highly crosslinked polyethylene articulation, dual mobility total hip designs were adopted by their pioneers in France. However, dual mobility implants are not without their own unique set of complications and concerns. First there is the issue of cost; these implants comprise more moving pieces, which inevitably increases implant cost, as well as the expense of inventory. This has led to a limited implementation of the dual mobility prosthesis in certain patients who are at an increased risk of dislocation (for any number of reasons, most commonly revision). Given multiple sites of mobility and the limited long-term follow-up of this prosthesis, its use has been controversial in younger or more active patients. Moreover, this implant is still subject to a standard mechanism of dislocation of the large polyethylene from the metal acetabular shell (which can be treated with closed reduction), but is also susceptible to the unique intraprosthetic dislocation of the smaller diameter femoral head from the polyethylene shell, which requires an open surgical procedure to treat. This is noted to occur in approximately 5% of patients.

Thus, a major issue is the persistent risk of dislocation after primary or revision total hip replacement, as outlined above. Again, the best implants at obviating this complication were the large diameter metal-on-metal prostheses, because with a large jump distance and high head to neck offset these implants afforded remarkably low dislocation rates. However, as prominently outlined in the media, these implants have fallen out of favor due to their own unique complications. Dual Mobility or "unconstrained tripolar" implants are an attempted hybrid of the large diameter implants, which avoid the catastrophic failures associated with metal wear particles. These implants are expensive, require a large inventory, and have a multitude of their own unique failure mechanisms. A dual mobility or unconstrained tripolar cup comprises more components with an increase in number of articulations, which carries an increased risk of wear at each additional articulation and also an increased risk of failure at each articulation. Not surprisingly, the smaller articulation of the dual mobility implants is susceptible to so called "retentive failure." This form of failure is unique to the dual mobility implants. It occurs when impingement of the prosthetic neck upon the larger outer diameter polyethylene shell causes wear that allows the smaller inner diameter femoral head component to dislocate. As stated earlier, this has been reported to occur in 5% of patients, and requires a trip to the operating room for open surgical reduction of the dislocation, as opposed to the standard prosthetic dislocation which typically can be treated closed.

Numerous publications are available that describe in general the current state of the art of hip arthroplasty and associated problems, including the foregoing problems, while other publications describe various efforts and strategies to overcome some of said problems. In that regard, following is a list of some representative publications: Van der Merwe, J. M., *J. Am. Acad. Orthop. Surg.*, 26(14):479-488 (2018, Jul. 15); De Martino, I., et al., *World J. Orthop.*, 5(3):180-187 (2014, Jul. 18); Stryker Technical Publication "MDMX3 Surgical Technique," https://www.strykermededed-.com/media/1286/mdm-x3-surgical-technique.pdf; Harris, W. H., et al., US Patent Application Publication No. 2002/0156536A1; Bar-Ziv, Y., US Patent Application Publication No. 2006/0259148A1; Steinberg, A., US Patent Application Publication No. 2003/0120347A1; Weeden, S. H., US Patent Application Publication No. 2014/0094927A1; Rahaman, M. N., et al., U.S. Pat. No. 8,357,205 (2013); Chinese Patent No. CN105030378B (2015).

Accordingly, there is an ongoing need for simple and versatile hip arthroplasty implants that overcome the foregoing problems, particularly the problem of dislocation. Disclosed in the following is a solution to the foregoing shortcomings via a simple, practical, economical design for an implant comprising an artificial femoral head and associated attachments of said femoral head to a femoral stem. More specifically, a primary emphasis of this invention is solving the issue of dislocation that continues to be problematic in hip arthroplasty.

SUMMARY OF INVENTION

In one embodiment, the present disclosure provides new alternative designs for a femoral head component that would cut in half the number of articulations of the dual mobility head component mentioned in the foregoing. In one aspect, one of the alternative designs comprises an all-polymeric (e.g., polyethylene; see below) large diameter femoral head component of spherical or spheroidal shape mated (not in an articulating manner) to a connector means. Said connector means is typically a metal (e.g., titanium) sleeve that comprises a female taper meant to affix to the male end of metal femoral neck component (i.e., trunnion). This titanium sleeve could have any of a number of taper configurations including $12/14$, $11/13$, $10/12$, or $14/16$; preferably the taper is a $12/14$ taper. This titanium female taper component is to be mated to the larger polyethylene spherical or spheroidal head in a non-modular manner. Illustratively, this female taper may be a Morse taper or bore or female side of the Morse taper or metallic bore comprising the female side of a Morse taper mating mechanism. (For example, see: Hernigou, P., et al., "One Hundred and Fifty Years of History of the Morse Taper: From Stephen A. Morse in 1864 to Complications Related to Modularity in Hip Arthroplasty," *International Orthopaedics*, 37:2081-2088 (2013)). Said all-polymeric large diameter femoral head component is designed to be attached via the connector means and trunnion to any of the various stem portions known in the art that penetrate into the bone of a femur of a patient. Said all-polymeric femoral head component may be constructed from one or more very tough, resilient polymeric materials that are highly resistant to wear; illustrative of these polymeric materials are various polymers described below. Said connector means may, illustratively, be constructed of one or more metallic materials compatible with human tissue, such as titanium, or other metals as described below; preferably, the metallic material is titanium. In a way, this new design essentially recreates the single large diameter articulation of the metal-on-metal prosthesis without the second site of articulation or mobility and without the dreaded metal-on-metal articulation. This new design decreases the potential sites of wear, increases the functional head size, increases the head-neck offset, and eradicates the risk of intraprosthetic dislocation or "retentive failure." Not only does this implant design have less risk of the aforementioned failures, but it will potentially be cost saving, and would help decrease inventory.

In another embodiment, the present disclosure provides an inventive hip arthroplasty implant, characterized by its simplicity, which comprises a novel femoral head portion (or head component) useful for total or partial hip replacement. Said femoral head portion also comprises a connector means via which the femoral head portion is mated to various femoral stem portions known in the art that penetrate into the bone of a femur of a patient. In one aspect, the implant is designed to be non-modular, so as to eliminate unnecessary articulating parts, and to reduce the overall cost and provide greater predictability. In another aspect, the implant's novelty lies in the all-polymeric surface of the head portion allowing for larger diameter heads, a feature that reduces the chances for dislocation of the hip arthroplasty. In another aspect, the femoral head of the implant is a non-mobile bearing femoral head with said all-polymeric surface. In another aspect, said polymeric surface is constructed from a very tough, resilient polymeric material that is highly resistant to wear. Thus, said polymeric material is a relatively rigid material compatible with human tissue, and may have shock absorbency and/or load-carrying properties. Examples of said polymeric material may include materials known in the art as highly cross-linked polyethylene, ultra-high molecular weight polyethylene (or "UHMWPE"), radiation treated UHMWPE having substantially no detectable free radicals (or "RT-UHMWPE"), polyether ether ketone (or "PEEK"), carbon reinforced PEEK, polyanhydrides, alpha polyesters, polyurethanes, and the like, or any other suitable polymeric materials compatible with human tissue and possessing one or more characteristics of toughness, resiliency, wear-resistance, rigidity, shock-absorbency and/or load-bearing properties. Preferably said polymeric material should have a modulus that is closer to the modulus of bone than to the modulus of a metal or a ceramic. It is contemplated herein that said polymeric material may comprise not only one, but two or more different polymeric materials. Preferred polymeric materials for the invention herein are highly cross-linked polyethylene, UHMWPE, and RT-UHMWPE, generally referred to hereinafter with the collective term "polyethylene." More preferred polymeric material for the invention herein are UHMWPE and RT-UHMWPE. The inventors are not aware of any femoral head design to date constructed totally from said "polyethylene" of the invention herein, and suspect that this is likely due to the historical concern of volumetric wear with earlier, inferior generations of polyethylene. However, with the advent of the advanced polyethylenes used in hip arthroplasty in the past 15-20 years, such as those of the invention herein (e.g., highly cross-linked polyethylene, UHMWPE, and RT-UHMWPE), while there remains concern about volumetric wear, to date these advanced polyethylene materials have remained remarkably resilient to this failure mechanism.

In another embodiment, the implant disclosed herein may comprise a femoral head portion that is formed solely of solid polymeric material constructed from one or more of the polymeric materials described in the immediately preceding paragraph, and also comprising a connector means for mating said femoral head portion to a femoral stem.

In another alternative embodiment, the implant disclosed herein may comprise a femoral head portion that includes a polymeric outer shell and a non-polymeric core; wherein the polymeric outer shell may be formed of solid polymeric material constructed from one or more of the polymeric materials described above; and wherein the non-polymeric core may be constructed from one or more metallic materials compatible with human tissue, illustratively including titanium (Ti), chromium (Cr), cobalt (Co), cobalt chrome, stainless steel, oxidized zirconium, or combinations thereof, and the like, or, alternatively, the non-polymeric core may be constructed from one or more ceramic materials or one or more ceramic-on-metal materials compatible with human tissue; and, wherein the polymeric outer shell and the non-polymeric core are fixedly attached to each other in a non-articulating manner, via one or more attachment methods as described in subsequent sections below. The polymeric outer shell may have a thickness in the range of between about 30 mm and about 4 mm, preferably between about 30 mm and about 6 mm, and most preferably between about 30 mm and about 8 mm.

In one key aspect, part of the surface of any of the alternative femoral head portions of the implant disclosed herein (i.e., those described in the foregoing or in the following) may be shaped in such a way so as to mate with the acetabular shell or acetabular cup in the hip socket of the pelvis of a patient and articulate to form a ball and socket joint. Accordingly, said part of the surface is formed in a spherical or spheroidal shape with a curvature having a diameter sized similar to or slightly less than the diameter of the acetabular shell or acetabular cup in the pelvis. The diameter of any of said femoral head portions of the implant may be in the range of between about 35 mm and about 70 mm, preferably between about 40 mm and about 64 mm, and most preferably between about 42 mm and about 58 mm. Further details are described in subsequent sections below.

In another embodiment, the implant disclosed herein comprises a connector means (as described in the foregoing) in any of the femoral head portions described above, wherein the connector means may be constructed of material that comprises a suitable biocompatible metal or a combination of metals, illustratively, the metallic materials described above (such as, but not limited to, titanium with or without cobalt chrome); and wherein the connector means is fixedly mated to the femoral head portion in a non-articulating manner, via one or more attachment methods as described in subsequent sections below.

Additional embodiments of the invention are described in the Detailed Description section below, and provide alternative designs of the femoral head portion of the invention herein, including designs comprising metallic spokes extending from the chamfer connector to the polymeric shell, metallic protrusions and/or circumferential equator ring(s) that provide interdigitation with the polymeric shell, and scaffolds press-fit into the polymeric shell.

The foregoing embodiments of the invention, and additional embodiments, are described in greater detail in the Detailed Description section below.

All publications cited throughout this application are incorporated herein by reference in their entirety. Indeed, throughout this description, it is to be understood that any and all publicly available documents described herein, including any and all cited U.S. patents, patent applications, and non-patent publications, are specifically incorporated by reference herein in their entirety. Nonetheless, the related art and publications described herein are not intended in any way as an admission that any of the documents described therein, including pending U.S. patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

Naturally, further objects, advantages and features of the present invention are disclosed throughout other areas of the specification, and will become apparent from the following detailed description, claims, and the accompanying drawings.

DESCRIPTION OF DRAWINGS

The foregoing summary, as well as the following detailed description of the preferred embodiments of the invention, will be better understood when read in conjunction with the accompanying figures, in which.

DETAILED DESCRIPTION

Before the present details of the invention are disclosed and described, it is to be understood that this invention is not limited to the specific components, methods, and implementation, or to the precise arrangements and instrumentalities shown, as such may, of course, vary while remaining within the scope and spirit of the invention. It is also to be understood that the terminology used herein is for the purpose of describing particular implementations only, and to assist in understanding the disclosure, and is not intended to be limiting.

The figures illustrating various aspects of the femoral head implant of the invention show some mechanical elements that partially or fully resemble standard mechanical elements used in the art and that will be recognized by one skilled in the art. The detailed descriptions of these elements are presented herein only to the degree necessary to facilitate an understanding of the novel features of the present invention.

Figure 1:
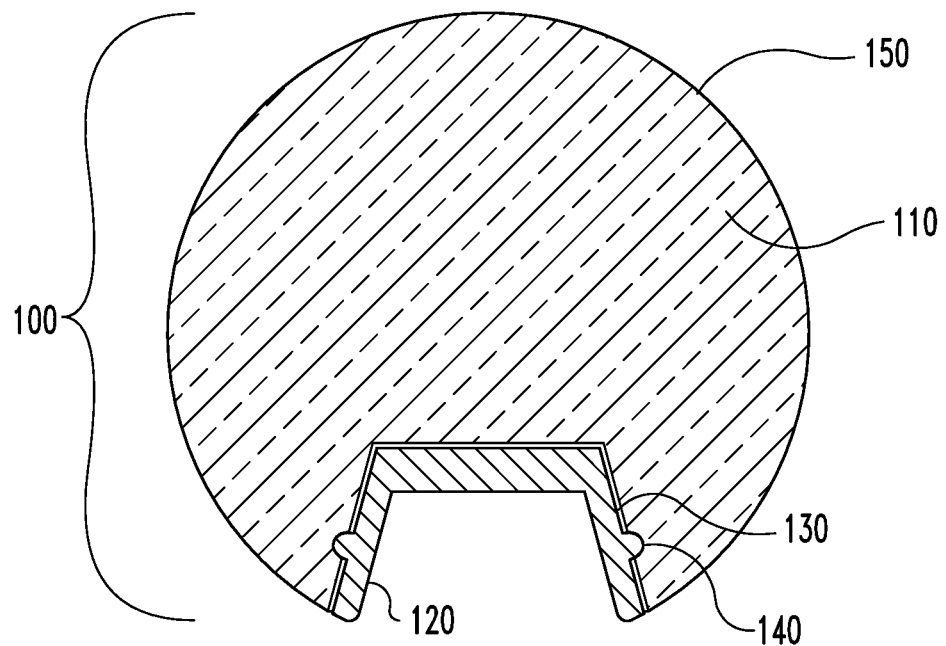
FIG. 1 is a cross-sectional side view depicting an illustrative femoral head portion of solid polymeric material, with a tapered metal connector attached at the bottom.

Referring to FIG. 1, presented is a cross-sectional side view depicting an illustrative, non-limiting embodiment of a femoral head portion of the invention, designated generally therein by the reference number 100 (referred to hereinafter as head portion 100). Head portion 100 includes a solid spherical or spheroidal shaped head 110 and a tapered connector 120 (also referred to in the foregoing as "connector means") attached and affixed to head 110 in a compatibly shaped cavity 130 at the bottom. The solid spherical or spheroidal shaped head 110 is constructed from a very tough, resilient polymeric material that is highly resistant to wear. Said polymeric material is a relatively rigid material compatible with human tissue, and may have shock absorbency and/or load-carrying properties. Examples of said polymeric material may include materials known in the art, such as, but not limited to, highly cross-linked polyethylene, UHMWPE, RT-UHMWPE, PEEK, carbon reinforced PEEK, polyanhydrides, alpha polyesters, polyurethanes, and the like, or any other suitable polymeric materials compatible with human tissue and possessing one or more characteristics of toughness, resiliency, wear-resistance, rigidity, shock-absorbency and/or load-bearing properties. Preferably said polymeric material should have a modulus that is closer to the modulus of bone than to the modulus of a metal or a ceramic. It is contemplated herein that said polymeric material may comprise not only one, but two or more different polymeric materials. Preferred polymeric materials for the invention herein are highly cross-linked polyethylene, UHMWPE, and RT-UHMWPE, generally referred to herein with the collective term "polyethylene." More preferred polymeric materials for the invention herein are UHMWPE and RT-UHMWPE. The tapered connector 120 may be constructed from one or more suitable metallic materials known in the art to be compatible with human tissue, such as the metallic materials described in the foregoing sections; illustrative of the metallic material that may be used for the connector 120 is Ti. The taper of connector 120 may be made similar to the taper of other connectors known in the art of joint arthroplasty, such as, illustratively, a $12/14$ taper, an $11/13$ taper, a $10/12$ taper, a $14/16$, or a C-taper; preferably the taper is a $12/14$ taper. The connector 120 additionally may include a multiplicity of protrusions 140 of various shapes extending into the solid polymeric material of head 110; the purpose of protrusions 140 is to affix the connector 120 to the solid polymeric material and prevent separation. Further affixing of the connector 120 to the solid polymeric material of head 110 may be achieved by using one or more methods known in the art, such as by using biocompatible screws and/or adhesives known in the art. The surface 150 of the spherical or spheroidal shaped head 110, and particularly the interfacing part of the surface that is intended to articulate with the acetabular shell or acetabular cup in the hip socket of the pelvis of a patient to form a ball and socket joint, is shaped to possess a curvature compatible for mating with the acetabular shell or acetabular cup, and is sized to have a diameter similar to or slightly less than the diameter of the acetabular shell or acetabular cup. Moreover, it is desirable that surface 150, or at least the interfacing part of the surface 150, may be designed to possess the degree of friction needed to provide stability of the patient and reduce the possibility of slips. The diameter of the spherical or spheroidal shaped head 110 of the implant may be in the range between about 35 mm and about 70 mm, preferably between about 40 mm and about 64 mm, and most preferably between about 42 mm and about 58 mm. Optionally, the head 110 may be provided with delimiting rails or grooves (not shown) that serve to define and limit the movement paths during articulation, and thus substantially prevent dislocation. Such limiting rails or grooves may also serve as "bumpers" to damp and cushion the femoral head at the limits of its articulation.

Figure 1A:
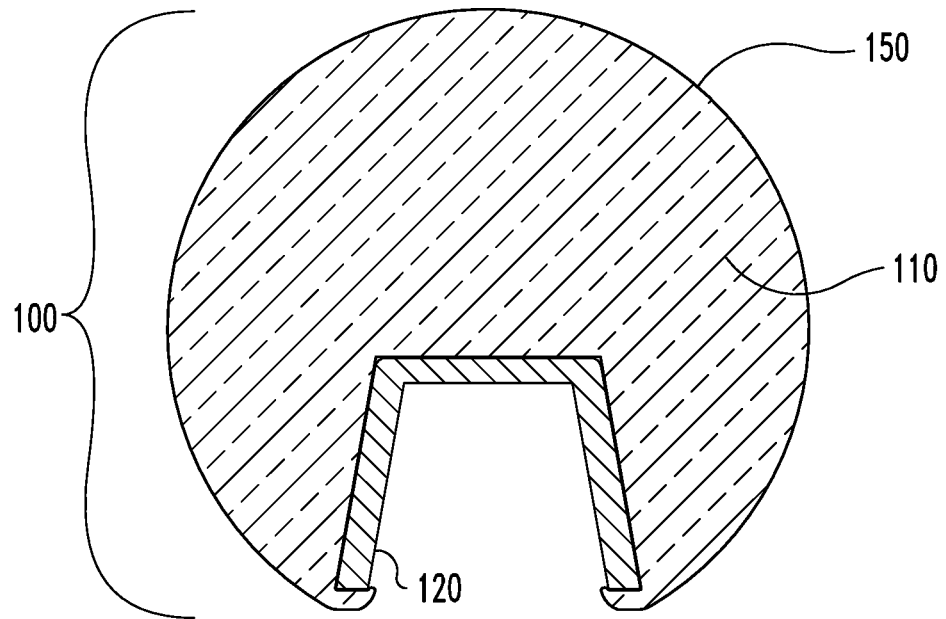
FIG. 1A is an alternative cross-sectional side view of the illustrative femoral head portion of FIG. 1. Not all the components and features of FIG. 1 are shown in FIG. 1A.

Referring now to FIG. 1A, presented is another cross-sectional side view depicting an alternative view of the head portion 100 of FIG. 1, described in the immediately preceding paragraph above, including the solid spherical or spheroidal shaped head 110 and a tapered connector 120. Not all the components and features of FIG. 1 are shown in FIG. 1A.

Figure 2:
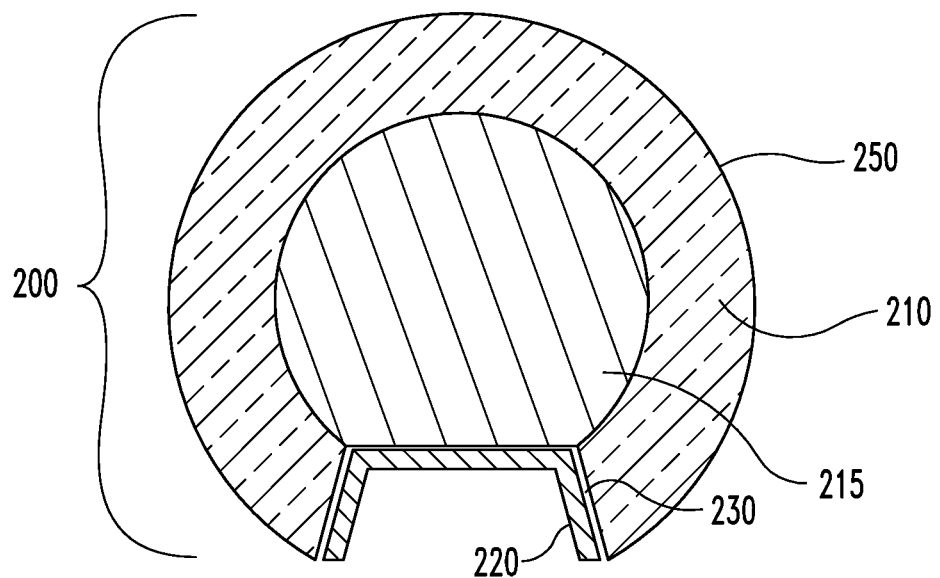
FIG. 2 is a cross-sectional side view depicting an illustrative femoral head portion that includes a polymeric outer shell and a non-polymeric core, with a tapered metal connector attached at the bottom.

Referring now to FIG. 2, presented is a cross-sectional side view depicting an illustrative, non-limiting embodiment of an alternative femoral head portion of the invention, designated generally therein by the reference number 200 (referred to hereinafter as head portion 200). Head portion 200 is very similar in overall shape and dimensions to the shape and dimensions of the above-presented head portion 100, and does likewise comprise a tapered connector 220 similar in all manner to connector 120 of the foregoing head portion 100; tapered connector 220 is preferably constructed of Ti or Cr, to reduce cost. Tapered connector 220 is attached and affixed at head portion 200 in a compatibly shaped cavity 230 at the bottom, and may include affixing protrusions (not shown), and further affixing may be achieved by using one or more methods known in the art, such as biocompatible screws and/or adhesives. The main difference between head portion 200 and head portion 100 is that head portion 200 comprises a polymeric outer shell 210 and a non-polymeric core 215. The polymeric outer shell 210 may be made up of one or more of the same polymeric materials described above for the polymeric materials of head portion 100, and possessing the same properties. The polymeric outer shell 210 may have a thickness in the range of between about 30 mm and about 4 mm, preferably between about 30 mm and about 6 mm, and most preferably between about 30 mm and about 8 mm. All the comments made above concerning surface 150 apply to surface 250 of head portion 200. The non-polymeric core 215 may be constructed from one or more metallic materials compatible with human tissue, illustratively including titanium (Ti), chromium (Cr), cobalt (Co), cobalt chrome, stainless steel, oxidized zirconium, or combinations thereof, and the like. For cost purposes, preferably the non-polymeric core 215 is constructed from Ti, Cr, or cobalt chrome. Alternatively, the non-polymeric core may be constructed from one or more ceramic materials compatible with human tissue, such as any of the ceramic materials used in joint arthroplasty, illustratively, alumina, zirconia, tantalum, and the like, or from ceramic-on-metal materials such as, illustratively, ceramic-on-cobalt-chromium material. The polymeric outer shell 210 and the non-polymeric core 215 are fixedly attached to each other in a non-articulating manner, via one or more attachment methods known in the art, such as by the use of biocompatible screws, adhesives, and the like.

Figure 2A:
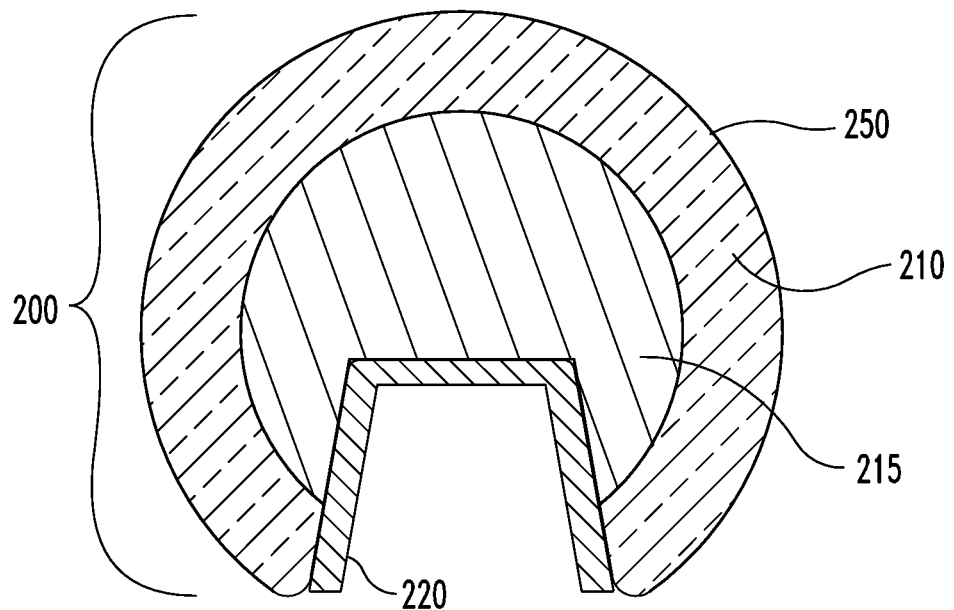
FIG. 2A is an alternative cross-sectional side view of the illustrative femoral head portion of FIG. 2. Not all the components and features of FIG. 2 are shown in FIG. 2A.

Referring now to FIG. 2A, presented is another cross-sectional side view depicting an alternative view of the head portion 200 of FIG. 2, described in the immediately preceding paragraph above, including the solid spherical or spheroidal shaped head 210, the tapered connector 220, the non-polymeric core 215, and surface 250. Not all the components and features of FIG. 2 are shown in FIG. 2A. Optionally, the tapered connector 220 may extend into the non-polymeric core 215, as shown in FIG. 2A.

Figure 3:
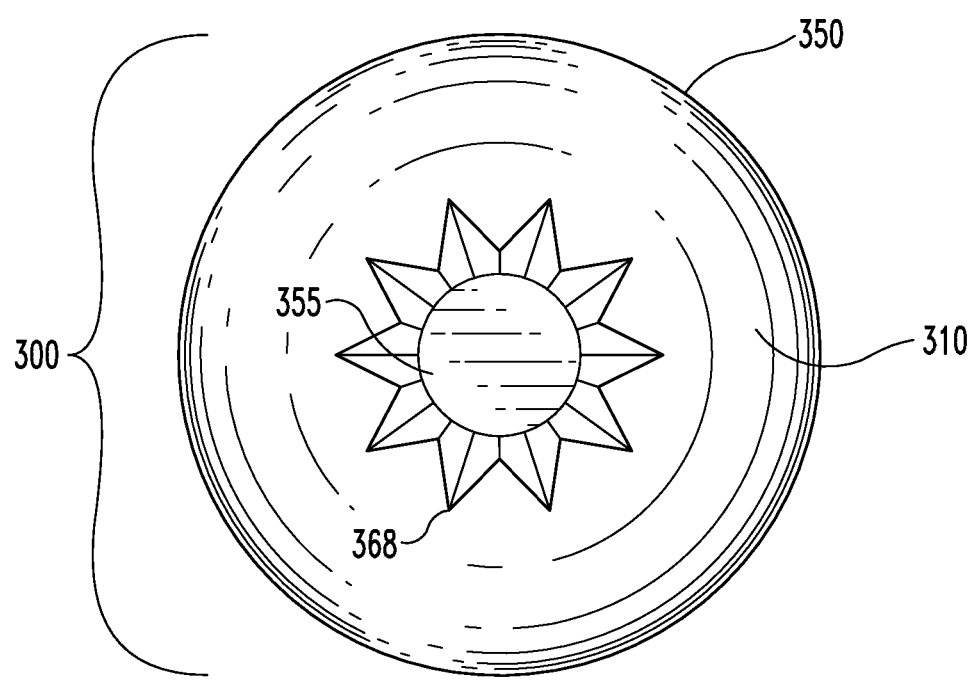
FIG. 3 is an axial bottom up view depicting an illustrative femoral head portion that includes a polymeric outer shell and a non-polymeric core, with a tapered metal connector attached at the bottom, having a metal femoral chamfer connector with metal protrusions interdigitating with the polymeric shell to prevent spinning of non-modular junction. The metal protrusions shown are for illustration only, and can have shapes and sizes that are different than the ones depicted in FIG. 3.

Referring now to FIG. 3, presented is an axial bottom up view depicting an illustrative, non-limiting embodiment of an alternative femoral head portion of the invention, designated generally therein by the reference number 300 (referred to hereinafter as head portion 300). Head portion 300 is very similar in overall shape and dimensions to the shape and dimensions of the above-presented head portions 100 and 200, and does likewise comprise a tapered connector 320 (not indicated in FIG. 3) similar in all manner to connectors 120 and 220 of the foregoing head portions 100 and 200; tapered connector 320 is preferably constructed of Ti or Cr, to reduce cost. Also shown in FIG. 3 are polymeric outer shell 310, and surface 350. Additionally, head portion 300 has a tapered metal femoral connector (or female chamfer connector) 355 with metal protrusions 368 interdigitating with the polymeric outer shell to prevent spinning of non-modular junction. The metal protrusions shown are for illustration only, and can have shapes and sizes that are different than the ones depicted in FIG. 3. Also, the polymeric shell to chamfer ratio shown in the figure is not necessarily to scale.

Figure 4:
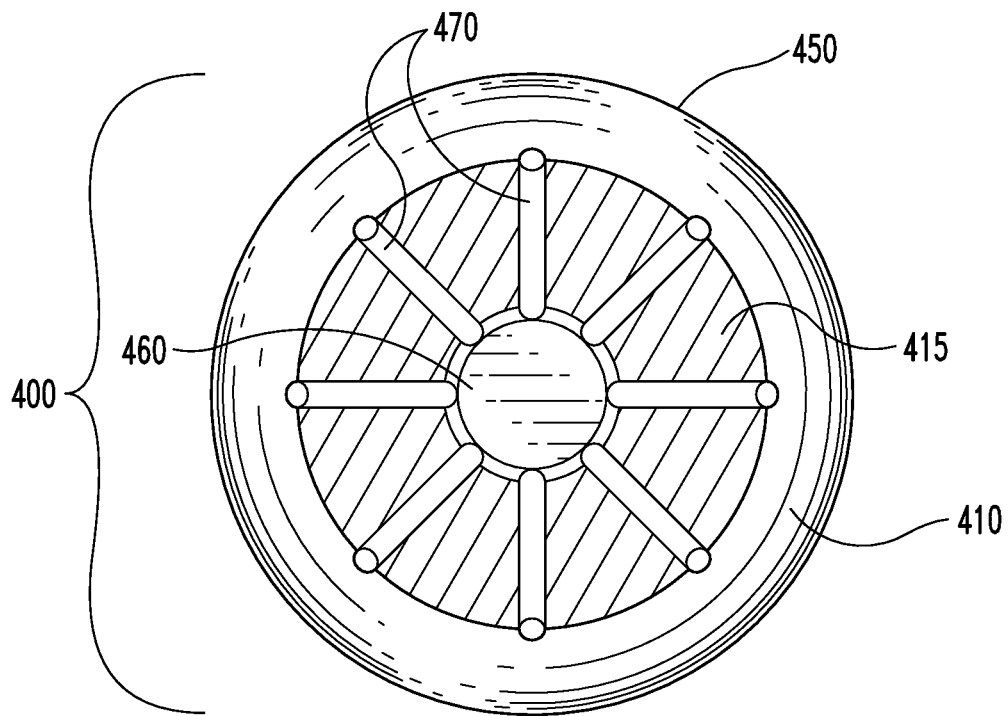
FIG. 4 depicts a view of an illustrative femoral head portion as viewed from the bottom up and into the chamfer connector and includes a polymeric outer shell and a non-polymeric core, comprising a multiplicity of spokes projecting from the chamfer and into the interior of the polymeric head portion to prevent spinning.

Referring now to FIG. 4, presented is an axial view as seen from the bottom up of an illustrative, non-limiting embodiment of an alternative femoral head portion of the invention, designated generally therein by the reference number 400 (referred to hereinafter as head portion 400). It includes a polymeric outer shell 410 and a non-polymeric core 415. Head portion 400 is very similar in overall shape and dimensions to the shape and dimensions of the above-presented head portions 100 and 200. All the comments made above concerning surface 150 apply to surface 450 of head portion 400. Head portion 400 likewise comprises a tapered connector (or female chamfer) 460 similar in all manner to connectors 120 and 220 of the foregoing head portions 100 and 200. Connector 460 may be made from any biocompatible metal similar to the metals described elsewhere herein. Included in the non-polymeric core 415 of this design is a multiplicity of spokes 470 projecting and radiating from the connector 460 and into the interior of the polymeric head portion; the purpose of the spokes 470 is to prevent spinning. The spokes 470 may preferably be constructed of biocompatible metal, but may also be constructed of certain suitable plastics. Also, the polymeric shell to chamfer ratio shown in the figure is not necessarily to scale.

Figure 4A:
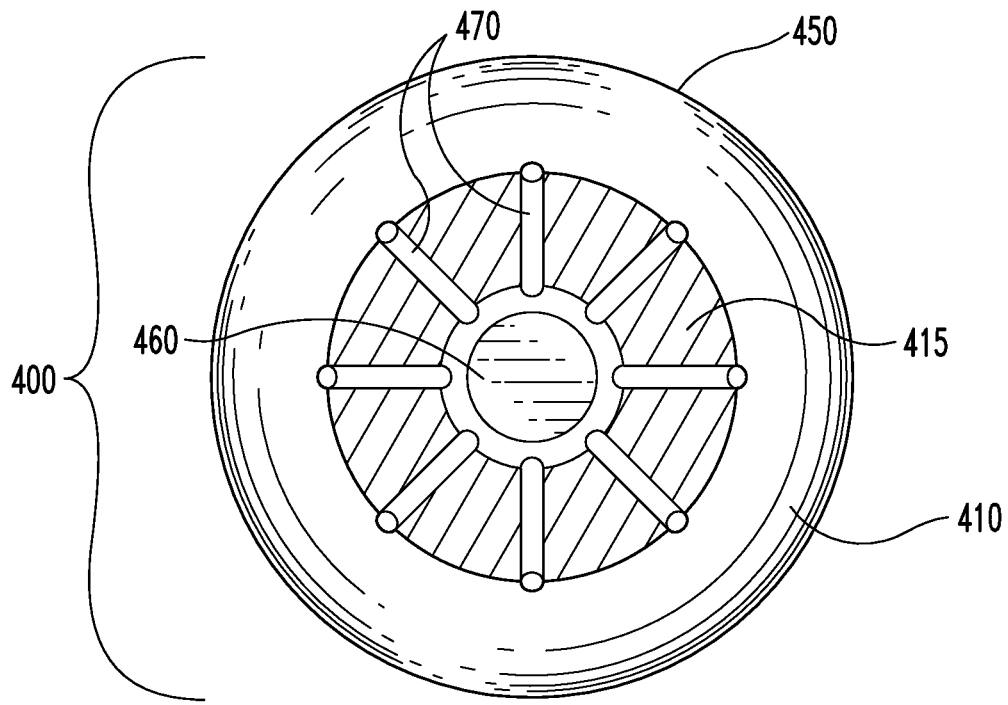
FIG. 4A depicts an alternative view of the illustrative femoral head portion of FIG. 4. Not all the components and features of FIG. 4 are shown in FIG. 4A.

Referring now to FIG. 4A, presented is another axial view as seen from the bottom up depicting an alternative view of the head portion 400 of FIG. 4, described in the immediately preceding paragraph above, including the polymeric outer shell 410, surface 450, the tapered connector 460, the non-polymeric core 415 including the multiplicity of spokes 470 projecting and radiating from the connector 460 and into the interior of the polymeric shell. Not all the components and features of FIG. 4 are shown in FIG. 4A.

Figure 5:
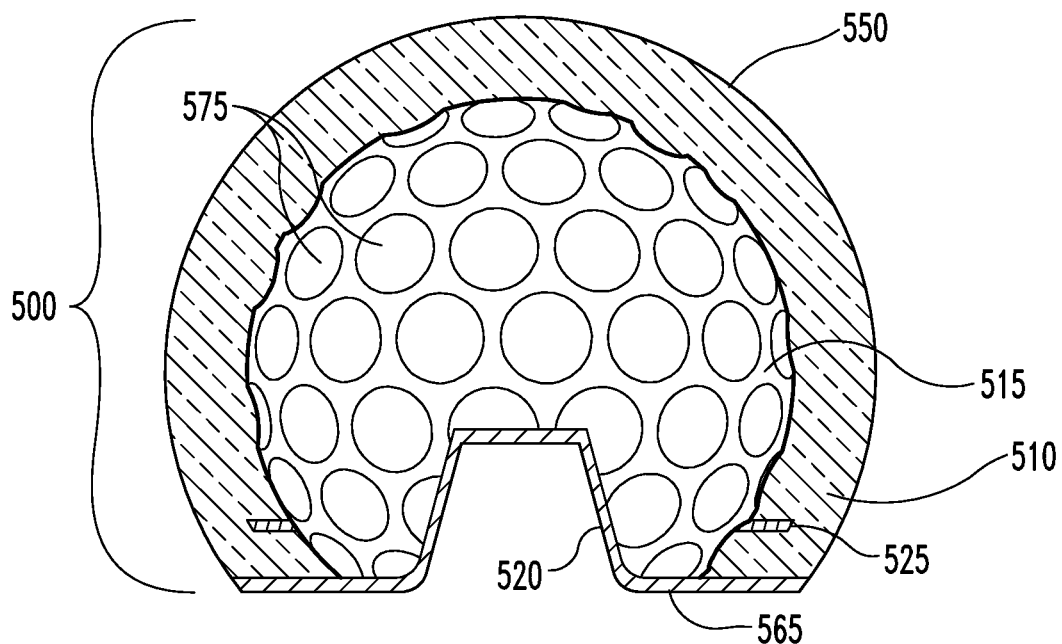
FIG. 5 is a cross-sectional side view depicting another illustrative femoral head portion of the invention that includes a polymeric outer shell and a non-polymeric core, with a tapered connector attached at the bottom of the non-polymeric core, also including pores for interdigitation to prevent spinning, an "equator" (or fins) to prevent run-in protrusion, and a "shoulder" to protect against dissociation.

Referring now to FIG. 5, presented is a cross-sectional side view depicting an illustrative, non-limiting embodiment of an alternative femoral head portion of the invention, designated generally therein by the reference number 500 (referred to hereinafter as head portion 500). Head portion 500 is very similar in overall shape and dimensions to the shape and dimensions of the above-presented head portions 100 and 200. Similar to head portion 200, head portion 500 includes a polymeric outer shell 510 and a non-polymeric core 515. All the comments made above concerning polymeric outer shell 210 and non-polymeric core 215, including the materials from which they are constructed, apply to polymeric shell 510 and non-polymeric core 515 of head portion 500. Likewise, all the comments made above concerning surface 150 apply to surface 550 of head portion 500. Head portion 500 does likewise comprise a tapered connector 520 similar in all manner to connectors 120 and 220 of the foregoing head portions 100 and 200. Additionally, head portion 500 comprises a circumferential metallic equator (or fins) 525, to serve the purpose of preventing the metal from subsiding into (or sinking into) the polymeric material. To prevent spinning, head portion 500 also comprises a multiplicity of "dimples" or pores 575; these provide interdigitation during manufacture of the head portion, as the melt polymeric material is manufactured directly onto the non-polymeric core to produce a "one-piece" head, wherein no articulation between the outer polymeric shell and the non-polymeric core occurs. Also, head portion 500 comprises a shoulder 565 to prevent against dissociation; shoulder 565 provides a "smoother transition", so that during manufacture the polymeric material comes up and over and envelopes the metal core.

Figure 5A:
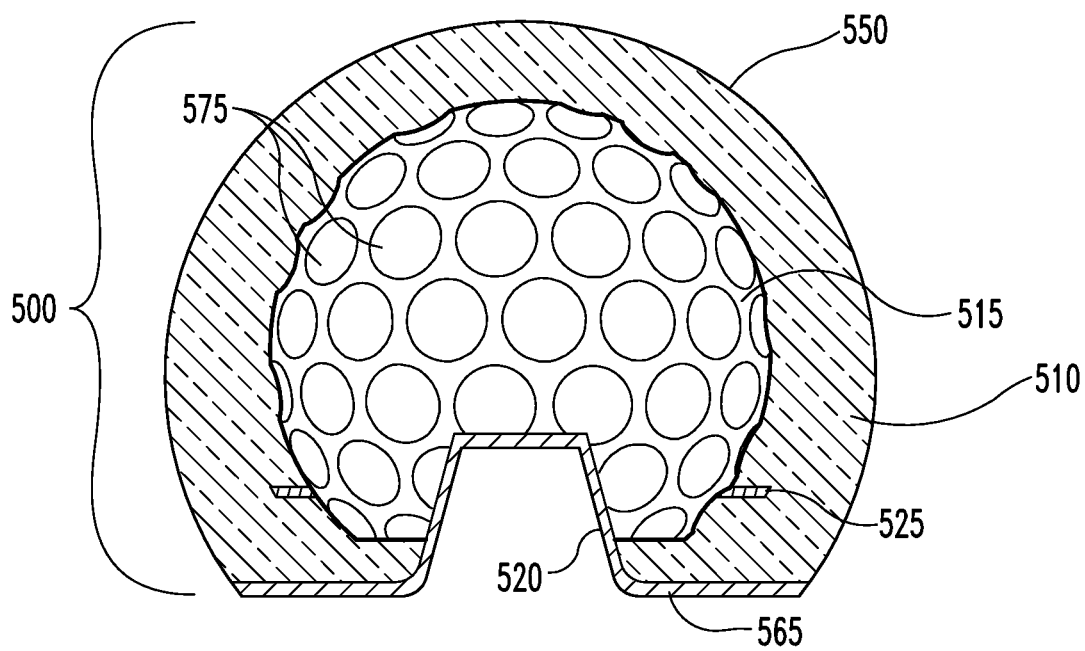
FIG. 5A is an alternative cross-sectional side view of the illustrative femoral head portion of FIG. 5. Not all the components and features of FIG. 5 are shown in FIG. 5A.

Referring now to FIG. 5A, presented is another cross-sectional side view of the head portion 500 of FIG. 5, described in the immediately preceding paragraph above, including the polymeric outer shell 510, surface 550, the tapered connector 520, the non-polymeric core 515, the circumferential metallic equator 525, and the shoulder 565. Not all the components and features of FIG. 5 are shown in FIG. 5A.

Figure 6:
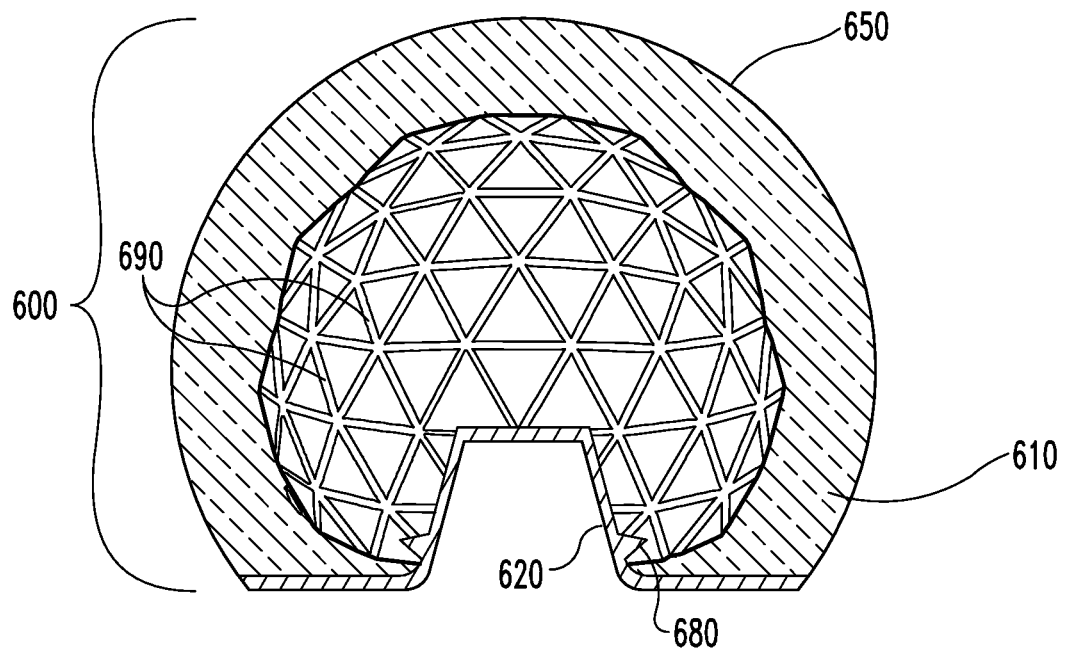
FIG. 6 is a cross-sectional side view depicting another illustrative femoral head portion of the invention that includes a polymeric outer shell and a metallic scaffolding that has been press-fitted into the polymeric outer shell during manufacture to prevent spinning, with a tapered connector attached at the bottom; the scaffolding also includes tines that send the spokes to the trunnion.

Referring now to FIG. 6, presented is a cross-sectional side view depicting an illustrative, non-limiting embodiment of an alternative femoral head portion of the invention, designated generally therein by the reference number 600 (referred to hereinafter as head portion 600). Head portion 600 is very similar in overall shape and dimensions to the shape and dimensions of the above-presented head portions 100 and 200. Similar to head portion 200, head portion 600 includes a polymeric outer shell 610, a surface 650, and a chamfer connector 620 made of metal, e.g., Ti. A metallic scaffolding 690 is affixed to the titanium chamfer connector 620 to provide internal structure and potentially decrease the overall thickness of the polymeric outer shell, and also to possibly increase the rigidity of the structure of the polymeric shell. Scaffolding 690 is press-fitted into the melt polymeric material of outer shell 610 during manufacture. All the comments made above concerning polymeric shell 210, including the materials from which it is constructed, apply to polymeric shell 610 of head portion 600. Likewise, all the comments made above concerning surface 150 apply to surface 650 of head portion 600. While FIG. 6 shows an illustrative geometrical design of the scaffolding 690, it is understood that scaffolds having other geometrical designs are contemplated herein. Scaffolding 690 may be made of any biocompatible metallic material used in the art, preferably a non-costly metal such as Ti; it serves as an alternative means to prevent spinning between the outer polymeric shell 610 and the non-polymeric core. Included as well in head portion 600 are a multiplicity of metallic tines 680 that send spokes to a trunnion (not shown), and thus connect the scaffolding to the polymeric outer shell and to the trunnion in the middle.

Figure 6A:
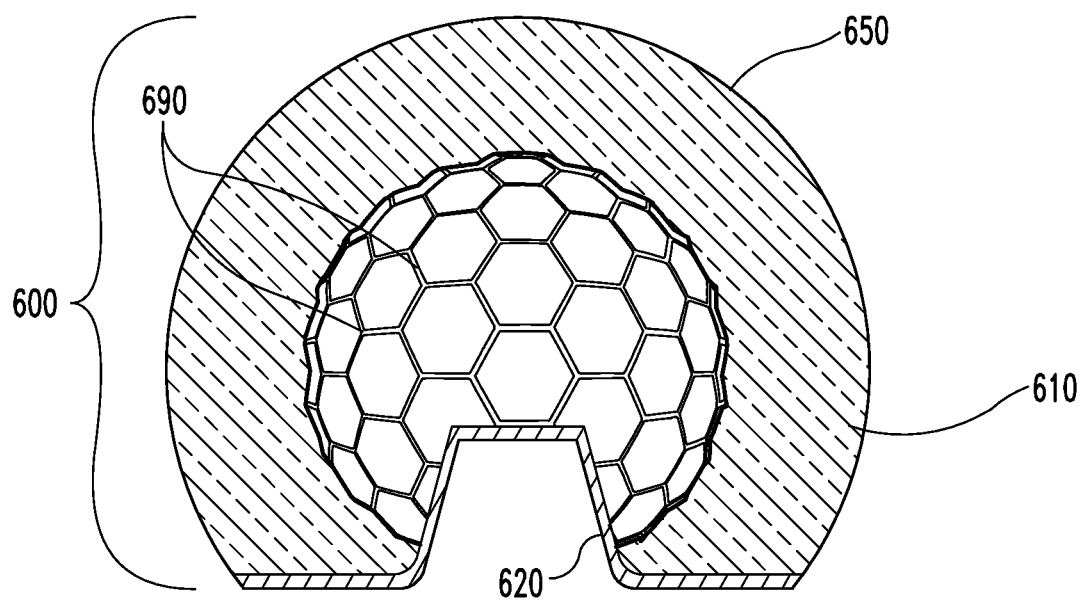
FIG. 6A is an alternative cross-sectional side view of the illustrative femoral head portion of FIG. 6. Not all the components and features of FIG. 6 are shown in FIG. 6A.

Referring now to FIG. 6A, presented is another cross-sectional side view of the head portion 600 of FIG. 6, described in the immediately preceding paragraph above, including the polymeric outer shell 610, surface 650, the tapered connector 620, and an alternative geometrical design of scaffolding 690. Not all the components and features of FIG. 6 are shown in FIG. 6A.

Figure 7:
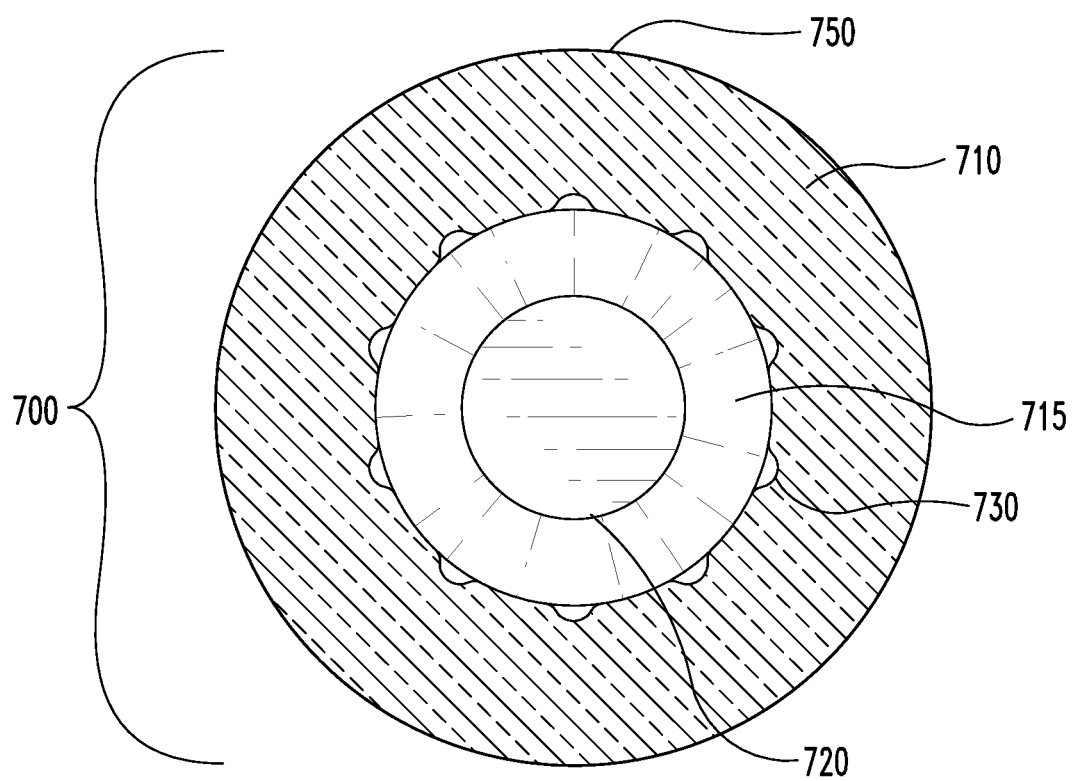
FIG. 7 depicts an axial view of another illustrative femoral head portion of the invention as viewed from the bottom up and into the chamfer connector and includes a polymeric outer shell and a non-polymeric core, comprising a multiplicity of bumps projecting from the non-polymeric core into the polymeric head portion to resist pull out.

Referring now to FIG. 7, presented is an axial view, as seen from the bottom up, of an illustrative, non-limiting embodiment of an alternative femoral head portion of the invention, designated generally therein by the reference number 700 (referred to hereinafter as head portion 700). It includes a polymeric outer shell 710 and a non-polymeric core 715. Head portion 700 is very similar in overall shape and dimensions to the shape and dimensions of the above-presented head portions 100 and 200. All the comments made above concerning surface 150 apply to surface 750 of head portion 700, and are not repeated here. The polymeric outer shell 710 may be constructed from any of the polymeric materials described earlier, such as UHMWPE and RT-UHMWPE. The non-polymeric core 715 may be constructed from one or more metallic and/or ceramic materials compatible with human tissue, illustratively including titanium (Ti), chromium (Cr), cobalt (Co), cobalt chrome, stainless steel, oxidized zirconium, or combinations thereof, and the like. For cost purposes, preferably the non-polymeric core 715 is constructed from Ti and/or ceramic. In one aspect, the polymeric outer shell 710 may be of one size, but may be of different thicknesses; while the non-polymeric core 715 may be of different sizes, and includes a female taper 720 (e.g., a Morse taper) that may be of different dimensions, e.g., a 12/14 taper, a C-taper, an 11/13 taper, and the like. The non-polymeric core snaps into the polymeric outer shell, and is prevented from pulling out via various shapes such as a multiplicity of "bumps" 730, and the like. Thus, in one of the embodiments contemplated herein, the polymeric outer shell snaps onto the non-polymeric core, e.g., a titanium female chamfer, and then becomes non-modular. This would allow the non-polymeric core to be fitted to engage with various femoral necks/stems known in the art, with different geometries, that could then snap onto various outer articular shells; the latter could also be of differing diameters. A clear advantage of this design is to limit inventory, as well as cost.

Figure 8:
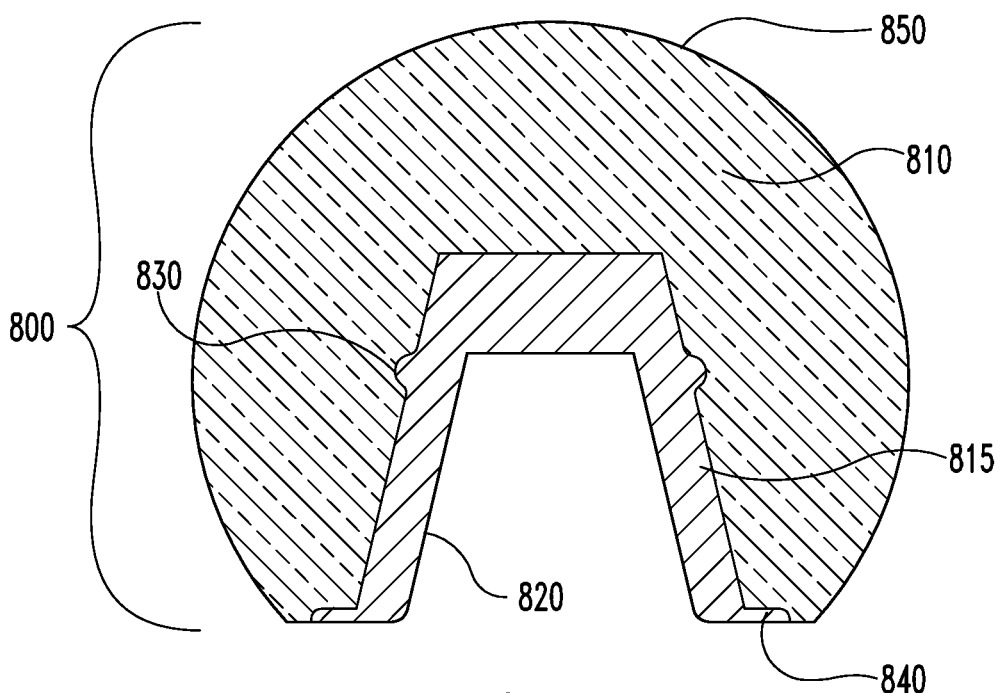
FIG. 8 is a cross-sectional side view depicting another illustrative femoral head portion of the invention similar to the head portion of FIG. 7; it includes an equator ring to resist pullout.

Referring now to FIG. 8, presented is a cross-sectional side view of a head portion of the invention, designated generally therein by the reference number 800 (referred to hereinafter as head portion 800), which is similar in many respects to the head portion 700 of FIG. 7 above. Thus, it includes a polymeric outer shell 810 having a surface 850, a non-polymeric inner core 815 having a tapered connector 820. The polymeric outer shell the non-polymeric inner core snap into each other. A protruding equator ring 830 in the inner core resists pullout of the polymeric outer shell and inner core from each other. Additionally, a multiplicity of "tabs" 840 protruding into the polymeric outer shell help to resist motion.

Figure 9:
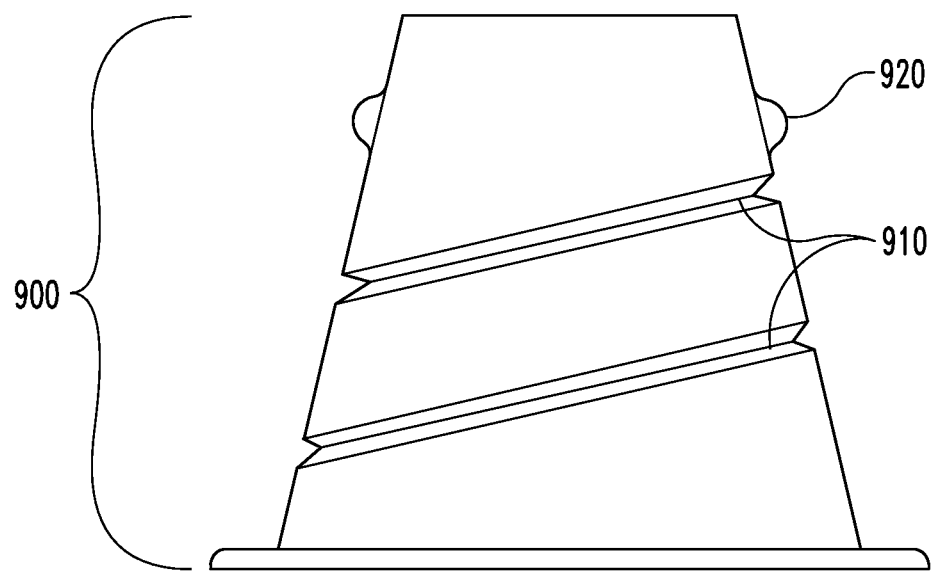
FIG. 9 is a side view depicting an illustrative non-polymeric core that snaps onto the polymeric outer shell, and includes a screw-on groove for engagement to the polymeric outer shell and an equator anti-pullout tab.

Referring now to FIG. 9, presented is a side view of an illustrative non-polymeric inner core 900 designed to snap into a polymeric outer shell of the invention, such as an outer shell similar to those described above for head portions 700 and 800. In this design, the non-polymeric inner core is constructed out of the same materials as the inner cores of head portions 700 and 800, and includes a female taper (not shown) as in the above. Inner core 900 may optionally include a screw-in thread (or groove) 910 to allow mating and engagement with the polymeric outer shell via twisting. Additionally, inner core 900 may include means that prevent pullout, such as the equator anti-pullout tabs 920 shown in FIG. 9, and the like.

It is understood that, as contemplated herein, additional femoral head designs may be made wherein various combinations of the components and features of the foregoing femoral heads and components 100-900 are comprised. Thus, additional femoral head designs are possible that comprise various combinations of, illustratively, a solid metallic and/or non-metallic core and/or combinations thereof, a multiplicity of spokes, scaffolding, interdigitating protrusions, and other of the internal components or features of femoral heads and components 100-900.

As a further example in support of some of the embodiments herein, such as the embodiment described in the foregoing for FIGS. 6 and 6A that includes scaffolding, submitted with this application are three exhibits, EXHIBIT A, EXHIBIT B, and EXHIBIT C. These three exhibits are images from three different perspectives of a prototype design that comprises a metallic core (e.g., titanium, ceramic, cobalt chrome, and the like) comprised of a single unit of a female taper centrally and surrounded by a structural scaffolding. The female chamfer is expressly intended for mating to a femoral stem, while the surrounding scaffolding would serve two purposes. The first purpose would be to provide support and structural integrity to the polymeric outer shell (e.g., polyethylene, etc.) that would comprise the outer articulations surface of the completed head. The second purpose would be to provide a lattice or scaffolding to allow the polymeric outer shell to be molded onto and, in some respects, into that scaffolding and lattice which would thereby coat the outer diameter in, e.g., polyethylene (or the like) to comprise the articulations surface of the implant; while the interdigitation would also ensure that the polyethylene and metal, once complete, comprise a non-modular unit such that the female chamfer and polymeric outer shell surface are unitized.

Thus, in one embodiment, disclosed herein is a prosthesis resembling the head of a human femur for use in total or partial hip arthroplasty of a patient in need of hip arthroplasty, said prosthesis comprising an artificial femoral head that includes: (a) a head portion that is constructed totally or partially of a polymeric material; (b) a metallic connector means having the shape of a female taper affixed in a similarly tapered cavity at the bottom of the head portion in a non-articulating manner; wherein said connector means is designed to connect said head portion in a non-articulating manner to a femoral stem portion configured to extend into and fixedly attach to the intramedullary canal of a femur; wherein said head portion has a spherical or spheroidal portion that has a diameter sized equal to or slightly smaller than the diameter of the acetabular cavity or cup of the pelvis of the patient, so as to allow the head portion to interface and articulate with the acetabular cavity or cup to form a ball and socket joint; wherein when said head portion is constructed partially of a polymeric material, said polymeric material forms a polymeric outer shell, and the head portion further includes an embedded core inside the polymeric outer shell, said embedded core comprising one or more of solid non-polymeric material, a multiplicity of metallic spokes, a metallic scaffolding, or a combination thereof, and where the head portion further comprises fixing means to fixedly attach the outer polymeric shell and the embedded core to each other to prevent articulation or separation, where the fixing means are selected from one or more biocompatible screws, adhesives, prongs, protrusions, fins, dimples, circumferential rings, and/or combinations thereof. In one aspect, said polymeric material is made of one or more materials selected from the following: highly cross-linked polyethylene, ultra-high molecular weight polyethylene ("UHMWPE"), radiation treated UHMWPE having substantially no detectable free radicals ("RT-UHMWPE"), polyether ether ketone ("PEEK"), carbon reinforced PEEK, polyanhydrides, alpha polyesters, and/or polyurethanes, and preferably selected from UHMWPE and/or RT-UHMWPE. In another aspect, when the embedded core is solid non-polymeric material, said non-polymeric material is constructed of one or more biocompatible metal selected from Ti, Cr, cobalt Co, cobalt chrome, stainless steel, oxidized zirconium, or combinations thereof, and preferably of Ti or Cr. In another aspect, when the embedded core is solid non-polymeric material, said non-polymeric material may be constructed of one or more biocompatible ceramic material is selected from alumina, zirconia, and/or tantalum. In another aspect, when the embedded core is solid non-polymeric material, said non-polymeric material may be constructed of one or more biocompatible ceramic-on-metal material selected from a ceramic-on-cobalt-chromium material or a ceramic-on-titanium material. In another aspect, when the embedded core comprises metallic spokes or metallic scaffolding, said metallic spokes or metallic scaffolding are made of a biocompatible metal selected from one or more of titanium, chromium, cobalt, cobalt chrome, stainless steel, oxidized zirconium, and/or combinations thereof. In another aspect, when the embedded core comprises metallic scaffolding, said scaffolding is press-fitted into the polymeric material of the polymeric outer shell. In another aspect, said connector means has a taper selected from a $12/14$, $11/13$, $10/12$, or $14/16$ taper, and preferably a $12/14$ taper, and is constructed of material comprising one or more biocompatible metal selected from Ti, Cr, Co, cobalt chrome, stainless steel, oxidized zirconium, or combinations thereof. In another aspect, said polymeric outer shell has a thickness in the range between about 30 mm and about 4 mm, preferably between about 30 mm and about 6 mm, and most preferably between about 30 mm and about 8 mm. In another aspect, the diameter of the spherical or spheroidal portion of said head portion may be in the range between about 35 mm and about 70 mm, preferably in the range between about 40 mm and about 64 mm, and most preferably in the range between about 42 mm and about 58 mm.

In another embodiment, disclosed herein is a method of use of the prosthesis of the invention herein in partial or total arthroplasty of the hip joint of a patient in need of repair, said method comprising the steps of: (a) affixing the head portion described above via the connector means described above to a femoral stem portion configured to extend into the intramedullary canal of a patient's femur; (b) carrying out a standard hip arthroplasty surgical technique to insert said femoral stem portion obtained in step (a) into the intramedullary canal of the patient's femur and fixedly attach said femoral stem portion in a manner that prevents articulation; and, (c) continuing the standard hip arthroplasty technique, resulting in repairing the patient's hip joint; wherein in step (a) the affixing of said head portion via said connector means to said femoral stem portion further includes the use of a trunnion.

As can be easily understood from the foregoing, the basic concepts of the present invention may be embodied in a variety of ways. The invention involves numerous and varied embodiments of making the joint arthroplasty prosthesis described herein. As such, the particular embodiments or elements of the invention disclosed by the description or shown in the figures accompanying this application are intended to be exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. When a value is expressed as an approximation by use of the antecedent "about," it will be understood that the particular value forms another embodiment. The term "about" generally refers to a range of numeric values that one of skill in the art would consider equivalent to the recited numeric value or having the same function or result.

It is to be understood that, as used herein, the grammatical conjunction "and/or" refers throughout to either or both of the stated possibilities.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Moreover, for the purposes of the present invention, the term "a" or "an" entity refers to one or more of that entity unless otherwise limited. As such, the terms "a" or "an", "one or more" and "at least one" can be used interchangeably herein.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed, or deemed to be admitted as prior art with respect to the invention.

The claims set forth in this specification are hereby incorporated by reference as part of this description of the invention, and the applicants expressly reserve the right to use all of or a portion of such incorporated content of such claims as additional description to support any of or all of the claims or any element or component thereof, and the applicants further expressly reserve the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification are further intended to describe the metes and bounds of a limited number of the preferred embodiments of the invention and are not to be construed as the broadest embodiment of the invention or a complete listing of embodiments of the invention that may be claimed. The applicants do not waive any right to develop further claims based upon the description set forth above as a part of any continuation, division, or continuation-in-part, or similar application.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. It will be apparent to one of ordinary skill in the art that various changes and modifications can be made to the claimed invention without departing from the spirit and scope thereof. In addition, all publications cited herein are indicative of the level of skill in the art and are hereby incorporated by reference in their entirety as if each had been individually incorporated by reference and fully set forth.

What is claimed is:

1. A prosthesis for resembling the head of a human femur for use in total or partial hip arthroplasty of a patient in need of hip arthroplasty, said prosthesis comprising an artificial femoral head that includes:
    (a) a head portion that is constructed partially of a polymeric material, the polymeric material forming a polymeric outer shell;
    (b) a metallic connector means having the shape of a female taper affixed in a similarly tapered cavity at the bottom of the head portion in a non-articulating manner;
    wherein said connector means is designed to connect said head portion in a non-articulating manner to a femoral stem portion configured to extend into and fixedly attach to the intramedullary canal of a femur;
    wherein said head portion has a spherical or spheroidal portion that has a diameter sized equal to or slightly smaller than the diameter of the acetabular cavity or cup of the pelvis of the patient, so as to allow the head portion to interface and articulate with the acetabular cavity or cup to form a ball and socket joint;
    wherein said head portion further comprises an interior cavity defined between the polymeric outer shell and the connector means and an embedded core interior to the polymeric outer shell within the interior cavity, said embedded core comprising one of a solid non-polymeric material, a multiplicity of metallic spokes, a metallic scaffolding, or combinations thereof, and where the head portion further comprises fixing means to fixedly attach the polymeric outer shell and the embedded core to each other to prevent articulation or separation.

2. The prosthesis of claim 1, wherein said polymeric material is made of one or more materials selected from the following: highly cross-linked polyethylene, ultra-high molecular weight polyethylene ("UHMWPE"), radiation treated UHMWPE having substantially no detectable free radicals ("RT-UHMWPE"), polyether ether ketone ("PEEK"), carbon reinforced PEEK, polyanhydrides, alpha polyesters, and polyurethanes.

3. The prosthesis of claim 2, wherein said one or more polymeric materials is selected from UHMWPE and RT-UHMWPE.

4. The prosthesis of claim 1, wherein when the embedded core is solid non-polymeric material, said non-polymeric material is constructed of one or more biocompatible metal.

5. The prosthesis of claim 4, wherein the one or more biocompatible metal is selected from Ti, Cr, cobalt Co, cobalt chrome, stainless steel, oxidized zirconium, or combinations thereof.

6. The prosthesis of claim 5, wherein the one or more biocompatible metal is selected from Ti or Cr.

7. The prosthesis of claim 1, wherein when the embedded core is solid non-polymeric material, said non-polymeric material is constructed of one or more biocompatible ceramic material.

8. The prosthesis of claim 7, wherein the one or more biocompatible ceramic material is selected from alumina, zirconia, tantalum, or combinations thereof.

9. The prosthesis of claim 1, wherein the embedded core is constructed of one or more biocompatible ceramic-on-metal material.

10. The prosthesis of claim 9, wherein the one or more biocompatible ceramic-on-metal material is a ceramic-on-cobalt-chromium material or a ceramic-on-titanium material.

11. The prosthesis of claim 1, wherein said metallic spokes or metallic scaffolding are made of a biocompatible metal selected from titanium, chromium, cobalt, cobalt chrome, stainless steel, oxidized zirconium, or combinations thereof.

12. The prosthesis of claim 1, wherein said scaffolding is press-fitted into the polymeric material.

13. The prosthesis of claim 1, wherein the connector means has a taper selected from a $12/14$, $11/13$, $10/12$, $4/16$ taper, or "C" taper.

14. The prosthesis of claim 1, wherein the connector means is constructed of material comprising one of biocompatible metal selected from Ti, Cr, Co, cobalt chrome, stainless steel, oxidized zirconium, or combinations thereof.

15. The prosthesis of claim 1, wherein said polymeric outer shell has a thickness in the range between about 30 mm and about 4 mm.

16. The prosthesis of claim 15, wherein said polymeric outer shell has a thickness in the range between about 30 mm and about 6 mm.

17. The prosthesis of claim 15, wherein said polymeric outer shell has a thickness in the range between about 30 mm and about 8 mm.

18. The prosthesis of claim 1, wherein the diameter of the spherical or spheroidal portion of said head portion is in the range between about 35 mm and about 70 mm.

19. The prosthesis of claim 18, wherein the diameter is in the range between about 40 mm and about 64 mm.

20. The prosthesis of claim 18, wherein the diameter is in the range between about 42 mm and about 58 mm.

21. A method for performing a partial or total arthroplasty of the hip joint of a patient in need of repair, said method comprising the steps of:
using the prosthesis of claim 1 to perform the partial or total arthroplasty.

22. The prosthesis of claim 1, wherein the embedded core comprises the metallic scaffolding press-fitted into the polymeric material.

23. The prosthesis of claim 22, further comprising a plurality of metallic tines that connect the metallic scaffolding to the polymeric outer shell.

24. The prosthesis of claim 1, where the fixing means comprise one of biocompatible screws, adhesives, prongs, protrusions, fins, dimples or other interdigitation between the embedded core and outer polymeric shell, circumferential rings, tines, or combinations thereof.

* * * * *